(12) United States Patent
Barbee et al.

(10) Patent No.: US 10,401,372 B2
(45) Date of Patent: *Sep. 3, 2019

(54) METHOD AND APPARATUS FOR AUTOMATED SAMPLE MANIPULATION

(71) Applicant: LIFE TECHNOLOGIES CORPORATION, Carlsbad, CA (US)

(72) Inventors: Kristopher Barbee, Pleasanton, CA (US); Maximilian Carpino, Uncasville, CT (US); Ray Wheeling, Nevada City, CA (US); Nicholas Peter Bajka, Meadow Vista, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/392,372

(22) Filed: Dec. 28, 2016

(65) Prior Publication Data

US 2017/0269109 A1  Sep. 21, 2017

Related U.S. Application Data

(60) Division of application No. 14/558,948, filed on Dec. 3, 2014, now Pat. No. 9,535,080, which is a continuation of application No. 13/543,758, filed on Jul. 6, 2012, now Pat. No. 8,920,751.

(60) Provisional application No. 61/532,884, filed on Sep. 9, 2011, provisional application No. 61/532,903, filed on Sep. 9, 2011, provisional application No. 61/505,770, filed on Jul. 8, 2011.

(51) Int. Cl.
*G01N 35/00* (2006.01)
*G01N 35/10* (2006.01)

(52) U.S. Cl.
CPC ..... *G01N 35/0098* (2013.01); *G01N 35/0099* (2013.01); *G01N 35/10* (2013.01); *G01N 35/1009* (2013.01); *Y10T 436/255* (2015.01)

(58) Field of Classification Search
CPC .............. G01N 35/10; G01N 35/1074; G01N 35/0098; G01N 35/0099; G01N 35/04; G01N 35/0412; G01N 35/0413; B01L 3/502
See application file for complete search history.

(56) References Cited

U.S. PATENT DOCUMENTS 5,055,408 A * 10/1991 Higo ................. G01N 35/0098
141/130
5,647,994 A    7/1997 Tuunanen et al.
6,033,574 A    3/2000 Siddiqi et al.
(Continued)

FOREIGN PATENT DOCUMENTS

EP    2333560    6/2011

OTHER PUBLICATIONS

PCT/US2012/045860, Invitation to Pay Additional Fees—Partial Search Report, Sep. 24, 2012, 1-8.

*Primary Examiner* — Brian R. Gordon

(57) ABSTRACT

The present teachings provide apparatuses and methods for automated handling of samples, e.g., biological or chemical samples. The apparatuses and the methods of the present teachings allow automated performance of various sample manipulation steps without manual intervention. In a preferred embodiment, the present teachings provide apparatuses and methods for automated enrichment of templated beads produced by PCR.

14 Claims, 5 Drawing Sheets

(56) References Cited

U.S. PATENT DOCUMENTS

| | | |
|---|---|---|
| 6,413,780 B1 | 7/2002 | Bach et al. |
| 8,562,920 B2 | 10/2013 | Tajima |
| 8,920,751 B2 | 12/2014 | Barbee et al. |
| 9,535,080 B2 | 1/2017 | Barbee et al. |
| 2005/0013741 A1 | 1/2005 | a'Brassard |
| 2005/0047963 A1 | 3/2005 | Safar et al. |
| 2006/0211080 A1 | 9/2006 | Frost et al. |
| 2007/0214900 A1 | 9/2007 | Porat et al. |
| 2008/0003571 A1 | 1/2008 | McKernan et al. |
| 2010/0137165 A1 | 6/2010 | Tajima |

\* cited by examiner

METHOD AND APPARATUS FOR AUTOMATED SAMPLE MANIPULATION

CROSS-REFERENCE TO RELATED APPLICATION(S)

This application is a divisional of U.S. application Ser. No. 14/558,948, filed Dec. 3, 2014, now U.S. Pat. No. 9,535,080 which is a continuation of U.S. application Ser. No. 13/543,758, filed Jul. 6, 2012, now U.S. Pat. No. 8,920,751, issued Dec. 30, 2014, which claims benefit of U.S. Provisional Application No. 61/505,770, filed Jul. 8, 2011, entitled "AUTOMATED ENRICHMENT FOR NUCLEIC ACID SEQUENCING", and naming inventor Kristopher Barbee, and claims benefit of U.S. Provisional Application No. 61/532,884, filed Sep. 9, 2011, entitled "METHOD AND APPARATUS FOR AUTOMATED SAMPLE MANIPULATION", and naming inventors Kristopher Barbee and Maximilian Carpino, and claims benefit of U.S. Provisional Application No. 61/532,903, filed Sep. 9, 2011, entitled "METHOD AND APPARATUS FOR AUTOMATED SAMPLE MANIPULATION", and naming inventors Kristopher Barbee, Maximilian Carpino, Ray Wheeling, and Mik Bajk, each of which is incorporated herein by reference in its entirety.

FIELD OF THE DISCLOSURE

The present teachings relate to an apparatus and method for automated handling of samples, e.g., biological or chemical samples, including automated performance of various sample manipulation steps without manual intervention.

BACKGROUND

A number of biological sample analysis methods rely on sample preparation steps as a precursor to carrying out the analysis methods. For example, a precursor to performing many biological sequencing techniques (e.g., sequencing of nucleic acid) includes amplification of nucleic acid templates in order to obtain a large number of copies (e.g., thousands or millions of copies) of the same template.

Polymerase chain reaction is a well understood technique for amplifying nucleic acids which is routinely used to generate sufficiently large DNA populations suitable for downstream analysis. Recently, PCR-based methods have been adapted to amplifying samples contained within emulsions for sequencing applications. In such amplification methods a plurality of biological samples (e.g. nucleic acid samples) may be discretely sequestered in microcapsules or droplets of an emulsion and PCR amplification conducted on each of the plurality of encapsulated nucleic acid samples simultaneously. Such microcapsules or droplets may be referred to as "microreactors" because the amplification reaction occurs within the microcapsule or droplet.

In some cases, the microreactor can include a template bead or particle which may serve as a support or carrier of amplified sample templates. The amplification process may be referred to as bead-based or particle-based emulsion amplification, for example, as described in US 2008/0003571 A1 to McKernan et al., which is incorporated herein in its entirety by reference. In such a technique, beads or particles along with DNA templates are suspended in an aqueous reaction mixture and then encapsulated in an inverse (water-in-oil) emulsion. The template DNA may be either coupled to the bead or particle prior to emulsification or may be included in solution in the amplification reaction mixture.

Emulsion amplification (e.g., ePCR) is a step in many next generation sequencing workflows. After ePCR is complete, the micro-reactors in the emulsion are broken, and the templated beads and nonamplifying beads are washed to remove the oil and emulsifiers. Enrichment is performed to separate templated beads from non-amplifying or poorly amplifying beads.

In a conventional enrichment step, polystyrene beads with a single-stranded adaptor attached are used to capture templated beads. The mixture of enrichment beads, enrichment bead-templated bead complexes, and non-amplifying beads is centrifuged. The enrichment step results in a layer of enrichment beads (with or without templated beads attached) at the top and a layer of non-amplifying beads at the bottom. The layer of enrichment beads is extracted and denatured to dissociate the templated beads from the enrichment beads. The enrichment step is performed manually, which is time consuming, with low yield and inconsistent quality of templated beads, and high cost.

It is therefore desirable to provide an automate enrichment process to enhance performance by minimizing complexity and cost of device and consumables, reduce hands on time, increase yield, achieve higher percentage of enriched particles, and minimize variability.

SUMMARY

The present teachings provide apparatuses and methods for automated handling of samples, e.g., biological or chemical samples. The apparatuses and the methods of the present teachings allow automated performance of various sample manipulation steps without manual intervention. In a preferred embodiment, the present teachings provide apparatuses and methods for automated enrichment of templated beads produced by PCR.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

Figure 1A:
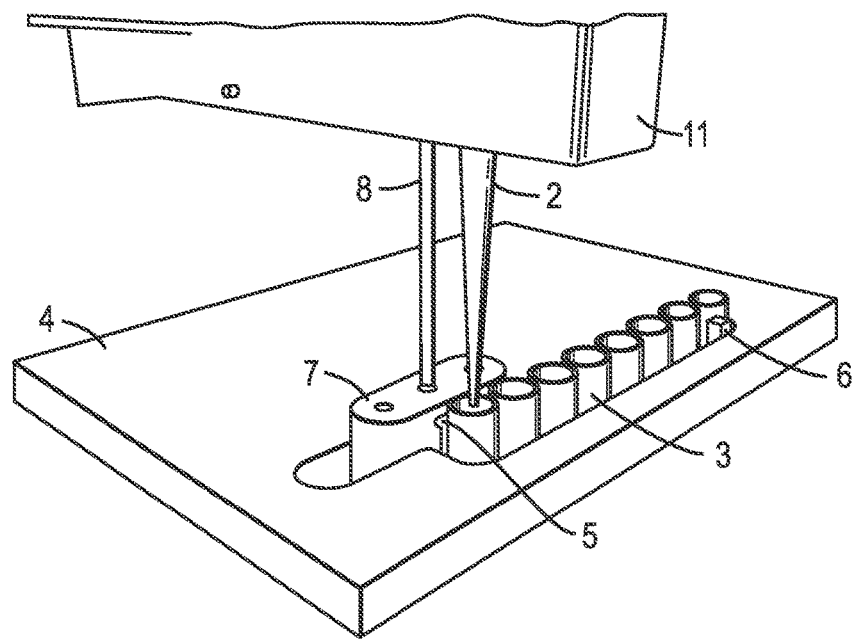
FIG. 1A is a perspective view of an automated sample handling system for conducting automated sample preparation according to various embodiments of the present teachings.

In various embodiments, the present teachings provide an apparatus for automated sample manipulation including (a) a platform having a plurality of sites adapted to hold each of a plurality of samples at each of said plurality of sites; (b) a magnet; (c) a mechanical stage or arm including a mount for a device having a compartment with an orifice, wherein the mechanical stage or arm is adapted to (c1) pick up the device; (c2) move the device to any of the plurality of sites and engage the device with a sample at the site; and (c3) move one or more samples on the platform via the device and a sample at an engaged site such that a sample is within a magnetic field of the magnet; (d) a pump connecting to the device; and (e) a control unit including a processor and memory encoding one or more programs, wherein said control unit is adapted to cause the mechanical stage or arm or the pump to carry out one or more tasks.

In various embodiments, the present teachings provide an apparatus for automated liquid sample manipulation, including (a) a platform having a plurality of sites adapted to hold each of a plurality of samples, a sample at each of the plurality of sites; (b) at least one magnet mounted on a block; (c) a mechanical stage or arm including (c1) a mount for a device having a compartment with an orifice; and (c2) a rod, wherein the mechanical stage or arm is adapted to (i) pick up the device, and move the device to any of the plurality of sites; and (ii) engage the rod to the block and move the magnet to or from one or more of the plurality of sites; (d) a pump connecting to the device; and (e) a control unit including a processor and memory encoding one or more programs, wherein the control unit is adapted to cause the mechanical stage or arm or the pump to carry out one or more tasks. The mechanical stage or arm may be adapted to slide the block such that the magnet is moved to or from a sample at a site at one end of the line of a plurality of sites.

In various embodiments, the present teachings provide an apparatus for automated liquid sample manipulation, including (a) a platform comprising a plurality of sites adapted to hold each of a plurality of samples at each of the plurality of sites; (b) at least one magnet mounted on a block, the block includes a rod; (c) a mechanical stage or arm comprising a mount for a device comprising a compartment having an orifice, wherein the mechanical stage or arm is adapted to (c1) pick up the device, and move the device to any of the plurality of sites; and (c2) engage the rod on the block and move the magnet to or from one or more of the plurality of sites; (d) a pump connecting to the device; and (e) a control unit including a processor and memory encoding one or more programs, wherein the control unit is adapted to cause the mechanical stage or arm or the pump to carry out one or more tasks. The mechanical stage or arm may be adapted to slide the block such that the magnet is moved to or from a sample at a site at one end of the line of a plurality of sites.

The apparatus of the present teachings may further include a holder for holding the device. The device may be a pipette. The platform may be a line of a plurality of sites adapted to hold an multi-well strip. The apparatus of the present teachings may comprise one magnet located at one end of the line of the plurality of sites. When the mechanical stage or arm moves the multi-well strip along the line, a sample at one end of the plurality of sites is within the magnetic field of the magnet. The apparatus of present teachings may also comprise a first and a second magnet located at opposite ends of the line of the plurality of sites. When the mechanical stage or arm moves the multi-well strip along the line, a sample at one end of the plurality of sites is within the magnetic field of the first magnet or a sample at the opposite end of the plurality of sites is within the magnetic field of the second magnet. The apparatus of the present teachings may further include a receptacle for a container to which a processed sample may be transferred.

In various embodiments, the present teachings provide the method for automated liquid sample manipulation, including (a) providing a plurality of samples at each of the plurality of sites, wherein each of the plurality of samples is held at one of the plurality of sites, wherein at least one sample of the plurality of samples comprises a nonmagnetic portion and a magnetic portion; (b) transferring one or more samples from one or more origin sites among the plurality of sites to a site holding the at least one sample comprising a nonmagnetic portion and a magnetic portion; (c) positioning the site holding the at least one sample comprising a nonmagnetic portion and a magnetic portion in a magnetic field of the magnet; and (d) separating the nonmagnetic portion from the magnetic portion by removing the nonmagnetic portion from the site holding the at least one sample comprising a nonmagnetic portion and a magnetic portion; wherein the steps (b)-(d) are performed without manual intervention. The nonmagnetic portion may comprise a liquid and the magnetic portion may comprise magnetic beads, and a separating step involves immobilizing the magnetic beads by a magnet and removing the liquid by aspiration.

The method of the present teachings may also include a step of (e) treating at least one sample having a nonmagnetic portion and a magnetic portion. The treating step may be any of degassing, mixing, heating, or stirring. The method may also include repeating the steps (b), (c), (d) or (e) in a predetermined sequence to effect separation of the templated beads from other components of the sample.

In various embodiments of the present teachings, the magnetic beads may be templated beads produced in emulsion PCR. The magnetic beads may be magnetic enrichment beads, complexes of magnetic enrichment bead and templated beads, and non-amplifying beads.

The present teachings apply to apparatuses and methods for automated handling of samples. The apparatuses and methods of the present teachings allow automated performance of various sample manipulation steps such as sample transfer, separation, and treatment, e.g., degassing, mixing, heating, and stirring, without manual intervention. In a preferred embodiment, the present teachings provide apparatuses and methods for automated enrichment of templated magnetic beads produced by PCR.

In various embodiments, the present teachings provide an apparatus which may comprise a holding means comprising a plurality of sites adapted to hold a plurality of samples each at one site, a transfer means for transferring one or more samples from one or more origin sites among the plurality of sites to one or more destination sites among the plurality of sites, a separation means for separating each of one or more samples at one or more separation sites among the plurality of sites into a plurality of different fractions, a positioning means for positioning the separation means and the samples at the separation sites by causing the separation means and the samples at the separation sites to be engaged for separation or disengaged, and a control means for controlling the transfer means, the separation means, and the positioning means by causing them to perform their respective functions.

In various embodiments of the apparatus, the holding means may be a horizontal surface that may optionally be flat or shaped or slotted so as to securely accommodate the samples. For example, the holding means may be a device comprising a platform, a table, a tray or the like.

The number and arrangement of the sites is not particularly limited. Various embodiments may include a one or two-dimensional array with X by Y number of sites where X corresponds to the number of samples to be manipulated by one automated process. In a specific embodiment, X is one, and the array is a one-dimensional array, e.g., a strip. Thus, the Y dimension corresponds to the number of sites for one sample manipulation process, e.g., the number of reagents, solutions, buffers, washes, solvents, destination sites, waste reservoirs or various other materials needed in accordance with the procedure to be automated by the apparatus. Each of the materials used in the process are contained in a suitable container, e.g., a sample well, tube, cuvette or the like. The sites/strips may or may not be attached to each other. The volume of the container may vary along the Y dimension in accordance with the amount of material needed in various stages of the sample manipulation. For example, for each sample, there are a finite number of Y sites that may each have a unique volume in accordance with the prescriptions of a particular automated manipulation procedure. In various embodiments, Y may be at least 2, 4, 8, 16, 32, or 64. In another embodiment, the array is a two-dimensional array having a plurality of one-dimensional arrays. For example, X can be at least 2, 4, 8, 16, 32, or 64. Such embodiments allow X automated manipulation processes to be carried out concurrently or in sequence.

The term "well" refers to a sample chamber or sample confinement area or region, which can be a physical or chemical attribute of a substrate that permit the localization of a sample of interest. A well may be a discrete region of a substrate. A well may be configured or associated with structural attributes such as hollows or wells having defined shapes and volumes which are manufactured into a substrate. The wells may have any suitable shape, such as square, rectangular, or octagonal cross sections, and may be arranged as a rectilinear array. Wells may also have hexagonal cross sections and be arranged as a hexagonal array, which permit a higher density of wells per unit area in comparison to rectilinear arrays. In some embodiments, the array may contain a total of 22, 23, 24, 25, 26 or 27. In other embodiments, the array of wells comprises 102, 103, 104, 105, 106 or 107 wells. Wells can also be a microtiter plate ("microplate"), which is a flat plate with multiple wells. The microplate can be a strip, e.g., an 8-well strip, or a two-dimensional array, e.g., an array of 12, 24, 48, 96, 384 or 1536 wells arranged in a X:Y rectangular matrix, e.g., a 2:3 rectangular matrix.

The one or two dimensional tray may be preloaded with various materials required for the sample manipulation procedure, for example, reagents, solutions, buffers, washes and solvents.

Various embodiments of the apparatus may include a transfer means for transferring one or more samples from one or more origin sites to one or more destination sites. An origin site is any site that contains a sample that is then transferred. A destination site is any site that a sample is transferred to. For example, a destination site may optionally be a separation site, a capture site or a sample treatment site. Separation, capture and sample treatment may also occur at the same site.

One example of a transfer means comprises a mechanical stage or arm that is capable of moving in one or more directions (e.g., a robotic stage or arm) which may optionally be detachable. The mechanical stage or arm may be capable of lateral and transverse motion so that all positions in a two dimensional array may be accessed. The mechanical stage or arm may also be capable of vertical motion, i.e., up and down. Alternatively, the up and down axis may be generally described as the Z axis or Z dimension. The mechanical stage or arm may also include a hinge joint enabling a tilting motion or a ball joint enabling rotational motion. A hinged joint enables an orifice of a transfer device to contact the bottom of a site at a slight angle so as to avoid the orifice from sealing along the bottom of the site.

The transfer means may include at least one transfer device that has an orifice and a compartment capable of accommodating at least the greatest volume of material required to be transferred in a single transfer step and containing this volume during transfer from an origin site to a destination site. The compartment can be, but is not limited to, a tube, a chamber, a vessel, or a cavity. The transfer device may be selected from, for example, a pipette, a needle, a tubing, a dropper, and the like. The transfer device may be fitted with or otherwise include a nozzle portion. In various embodiments the transfer means may include an array of transfer devices and is capable of multi-channel transfer. Preferably, the number of transfer devices corresponds to the number of concurrent or sequential manipulation processes to be performed, e.g., X. For example, each of a plurality of transfer devices is adapted to operate on one among the plurality of strips.

The transfer device can be disposed on the robotic arm, thus it is moved to any desired sample site. Other devices that can move the transfer device or the samples are also contemplated. For example, the transfer means may include a motorized device to move the platform so that a desired sample can be moved to the transfer device, while the robotic arm can move in the Z axis to engage or disengage the transfer device.

The transfer means may further include a mechanism for acquiring or discharging at least one volume of material. In various embodiments the mechanism for acquiring or discharging a volume of material may be by volume displacement. For example, the mechanism may be selected from a pump, a suction bulb, a plunger, a syringe, a diaphragm, a piston and the like. This mechanism may also be used as a sample treatment means for performing degassing, mixing, agitating, suspending particles and the like. The volume transferred by the transfer means can be controlled by the apparatus control means. The volume may optionally be unique for each transfer step.

In various embodiments the apparatus may further include a sample treatment means for performing various treatment steps such as degassing, mixing, heating, stirring and the like at a sample treatment site. The sample treatment means can comprise a transfer device and mechanism as described above in connection with the transfer means, a heating element such as a heating block or a heating coil, or a stirrer such as a mechanical stirrer or a magnetic stirrer.

Various embodiments of the apparatus may include a separation means for separating one or more samples at one or more separation sites. In various embodiments, the separation means may enable the separation of a multi-phase sample, e.g., a sample comprising a liquid fraction and a solid fraction of a sample at a separation site. In one embodiment, the sample comprises a liquid fraction and a solid fraction (e.g., solid particles in a solution), at least a portion of the solid fraction (e.g. at least some of the solid particles) is magnetic and the separation means comprises a magnet. Examples of a magnetic solid fraction include magnetic particles or beads. When the magnetic field of the magnet acts on a separation site, the magnetic solid fraction of the sample is sufficiently retained/held at the separation site so that the non-magnetic solid or liquid fraction of the sample can be separated from the magnetic solid fraction, for example by aspiration. The magnetic field may be a persistent magnetic field such as that generated by a permanent magnet, e.g., a bar magnet, or may be a temporary magnetic field such as that generated by an electromagnet, i.e., an electric current flowing through a conducting material such as a coiled wire e.g., a solenoid. In another embodiment, the sample comprises two or more immiscible liquid fractions. The separation means separates the different liquid fractions, e.g., by aspirating one liquid fraction. In other embodiments, the sample comprises both two or more immiscible liquid fractions and a magnetic solid fraction. The separation means separates these fractions by a combination of magnetic and liquid separation discussed above.

In various embodiments, the apparatus may further include a positioning means for positioning various components of the apparatus. For example, the positioning means can bring various components of the apparatus into an "IN" configuration and an "OUT" configuration. The IN and OUT configurations are characterized by whether the components can perform their respective functions.

For example, in one embodiment in which the separation means comprises a permanent magnet, the positioning means is configured to move a sample at a separation site or the magnet such that an IN configuration corresponds to a configuration in which the sample is within the magnetic field of the magnet, whereas an OUT configuration corresponds to a configuration in which the sample is outside the magnetic field.

In an embodiment in which the separation means comprises a permanent magnet, when the apparatus is in an IN configuration, the magnet is in proximity to a separation site such that the magnetic solid fraction at the separation site will be retained during a separation step. When the apparatus is in an OUT configuration, the magnetic is not near the separation site, i.e., the magnet is at a sufficient distance such that the magnetic solid fraction at the separation site will not be affected by the magnetic field. The distance between a separation site and a magnet in the IN or OUT configuration may depend on the strength of the magnetic field or the nature of solid magnetic fraction in the sample. A spatial relationships encompassing IN and OUT configurations is arranged such that (1) the solid magnetic fraction is sufficiently retained during separation when the apparatus is in an IN configuration, and (2) the solid magnetic fraction is sufficiently unaffected by the magnetic field such that it may be manipulated, e.g., stirred, mixed, suspended, or transferred from the separation site when the apparatus is in an OUT configuration.

However, the positioning means does not need to actually move the sample or the magnet. For example, in one embodiment in which the separation means comprises an electromagnet, the positioning means may be configured to turn on or off the magnetic field at a sample at a separation site such that an IN configuration corresponds to a configuration that the magnetic field is on, whereas an OUT configuration corresponds to a configuration in which the magnetic field is off.

In another example, a positioning means can move various components of the apparatus into a configuration so that the treatment means can act on a sample at a sample treatment site.

Various embodiments of the apparatus may also include a capture means adapted to capture one or more samples or fractions thereof at one or more capture sites among said plurality of sites. The capture means may include a capture magnet.

The positioning means may be an actuator, e.g., a stepper motor or solenoid, which can engage various components of the apparatus to be moved.

In various embodiments, the actuator can engage and move a magnet or an object containing a magnet into an IN position and an OUT position and can subsequently disengage.

In one embodiment, a rod extending from the transfer means can engage and move a magnet, or a block containing the magnet, into an IN position, i.e., placing the magnet adjacent to a separation site and can slide the block to an OUT position, i.e., placing magnet at a sufficient distance so that the magnet is not affecting the magnetic solid fraction. The actuator can disengage at either the IN or the OUT position so that various components of the apparatus are free to perform other tasks. In such an embodiment, the rod and the transfer means serve as the actuator.

In alternative embodiments, the actuator can engage and move a sample at a separation site relative to a magnet and into an "IN" position and an "OUT" position and can subsequently disengage. For example, a rod extending from a transfer means can engage and move a separation site into an IN position, i.e., placing the separation site adjacent to a magnet and can position the separation site into an OUT position, i.e., placing the separation site at a sufficient distance so that the separation site is not sufficiently affected by the magnetic field. The actuator can disengage so that various components of the apparatus are free to perform other tasks.

In another embodiment, the actuator may be a rod extending from the transfer means that engages and moves a sample into an IN position, i.e., placing the sample at a separation site adjacent to a magnet and can slide the sample to an OUT position, i.e., placing the sample at a separation site at a sufficient distance so that the magnet is not affecting the magnetic solid fraction.

In a preferred embodiment, the transfer device also serves as the actuator. For example, the transfer device may be a pipette that serves as an actuator that engages and moves a sample at a separation site towards or away from a magnet, e.g., into an "IN" or an "OUT" configuration. Alternatively, the pipette may serve as an actuator that engages and moves a magnet towards or away from a sample at a separation site, e.g., into an "IN" or an "OUT" configuration.

Various embodiments of the present teachings may include a control means for controlling a transfer means, a separation means, a positioning means, and optionally a sample treatment means and capture means. The control means may receive instructions and cause the transfer means to transfer samples, the positioning means to relatively position the separation means and sample, and the separation means to separate the samples. The control means may include a user interface for allowing a user to set one or more operational parameters. The control means can be programmed to perform a variety of transferring, positioning, separating and sample treatment steps on a plurality of samples without manual intervention. The control means may further include an electronic processing unit encoding various programs for controlling at least one of the transfer means, separation means, positioning means, sample treatment means and capture means.

An embodiment of the present teachings may include a computer program product, comprising a computer usable medium having a computer readable program encoded therein, the computer readable program adapted to be executed to implement a method using the apparatus according to the present teachings. The method comprises causing the transfer means to transfer one or more samples, causing the positioning means to positioning the separation means and one or more samples, causing the separation means to separate one or more samples, and optionally causing the sample treatment means to treat one or more samples or the capture means to capture one or more samples. In one embodiment, the computer program product further causes the apparatus to repeat these steps in any sequence without manual intervention.

Thus, an embodiment of the present teachings may include a computer-readable storage medium having executable instructions for performing the methods described above. The storage medium may be any type of computer-readable medium (i.e., one capable of being read by a computer), including non-transitory storage mediums such as magnetic or optical tape or disks (e.g. hard disk or CD-ROM), solid state volatile or non-volatile memory, including random access memory (RAM), read-only memory (ROM), electronically programmable memory (EPROM or EEPROM), or flash memory. The term "non-transitory computer-readable storage medium" encompasses all computer-readable storage media, but excludes a transitory, propagating signal. As explained above, the instructions on the computer-readable storage medium may control the operation of the apparatus of the present teachings.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements or software elements may vary in accordance with any number of factors, such as desired computational rate, power levels, heat tolerances, processing cycle budget, input data rates, output data rates, memory resources, data bus speeds and other design or performance constraints.

Some embodiments may be implemented, for example, using a computer-readable medium or article which may store an instruction or a set of instructions that, if executed by a machine, may cause the machine to perform a method or operations in accordance with the embodiments. Such a machine may include, for example, any suitable processing platform, computing platform, computing device, processing device, computing system, processing system, computer, processor, or the like, and may be implemented using any suitable combination of hardware or software. The computer-readable medium or article may include, for example, any suitable type of memory unit, memory device, memory article, memory medium, storage device, storage article, storage medium or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled or interpreted programming language.

Although described above separately, the present teachings contemplate that one or more of the transfer means, separation means, positioning means, sample treatment means and capture means may be implemented by one or more shared devices. For example, the transfer means and the positioning means may both comprise the same actuator which is configured to move the sample or the magnet.

The present teachings also provide a method for automated sample manipulation of a plurality of samples. In one embodiment, the method may comprise providing the plurality of samples each at one of a plurality of sites, transferring one or more samples from one or more origin sites among to one or more destination sites, and separating each of one or more samples at one or more separation sites into a plurality of different fractions. The transferring and separating steps are performed without manual intervention. In various embodiments, the method may repeat the transferring and separating steps in any sequence a plurality of times.

In one embodiment, at least one of the plurality of samples comprises a nonmagnetic portion and a magnetic portion, and the separating step may comprise immobilizing the magnetic portion and removing the nonmagnetic portion. In one embodiment, the nonmagnetic portion comprises a liquid, which may be a solution, and the magnetic portion comprises magnetic particles or beads. The separating step may comprise immobilizing the magnetic particles or beads by a magnet and removing the liquid by aspiration. In one embodiment, the magnetic beads comprise templated beads produced by PCR, e.g., by emulsion PCR. In one embodiment, the magnetic beads comprise magnetic enrichment beads, complexes of magnetic enrichment bead and templated beads, and non-amplifying beads. The method may further comprise a step treating one or more samples at one or more sample treatment sites. The treating step can comprise one or more of degassing, mixing, heating, or stirring. The method may comprise repeating the steps transferring, separating, and treating (such as one or more of degassing, mixing, heating, or stirring) in a predetermined sequence to achieve the object of the automated process, e.g., separation of the templated beads from other components.

In a preferred embodiment, the apparatus according to the present teachings is for automated liquid sample manipulation, and includes a platform holding eight 1×8 arrays, at least one magnet located near the end of the 1×8 array having a sample containing a magnetic portion to be separated, a mechanical stage or arm having a mount for holding a transfer device, e.g., a pipette, a pump connected to the transfer device and a control unit including a processor and memory encoding one or more programs. The control unit is adapted to cause the mechanical stage or arm and pump to carry out various tasks. The mechanical stage or arm is adapted to pick up the pipette; position the pipette at any of the plurality of sites and engage the transfer device with a liquid material at that site. The mechanical stage or arm is also adapted to use the transfer device to move the 1×8 array on the platform so that a sample is at a separation site such that the sample is within a magnetic field of said magnet.

In various embodiments of the present teachings, the method may be carried out as follows using an 8-well strip in which the user first loads sample and all reagents (including wash solution) into the strip wells. The apparatus of the present teachings is then set to perform the following sample manipulation sequence: 1) moving tip to well B and mixing solution via multiple aspirate/dispense cycles; 2) aspirating and transferring solution to well A; 3) mixing solutions in well A via multiple aspirate/dispense cycles; 4) actuating magnet, then aspirating and transferring solution to well G; 5) de-actuating magnet; 6) aspirating wash solution from well C and transferring to well A; 7) mixing solutions in well A via multiple aspirate/dispense cycles; 8) actuating magnet, then aspirating and transferring solution back to well C; 9) repeating wash cycle as in steps 6, 7 and 8 using wells D and E; 10) de-actuating magnet and moving tip to well F, aspirating/transferring solution to well A; 11) mixing solutions in well A via multiple aspirating/dispensing cycles; and 12) actuating magnet then aspirating and transferring solution from well A to well H. After the above steps, the user collects the processed sample in well H.

Figure 1B:
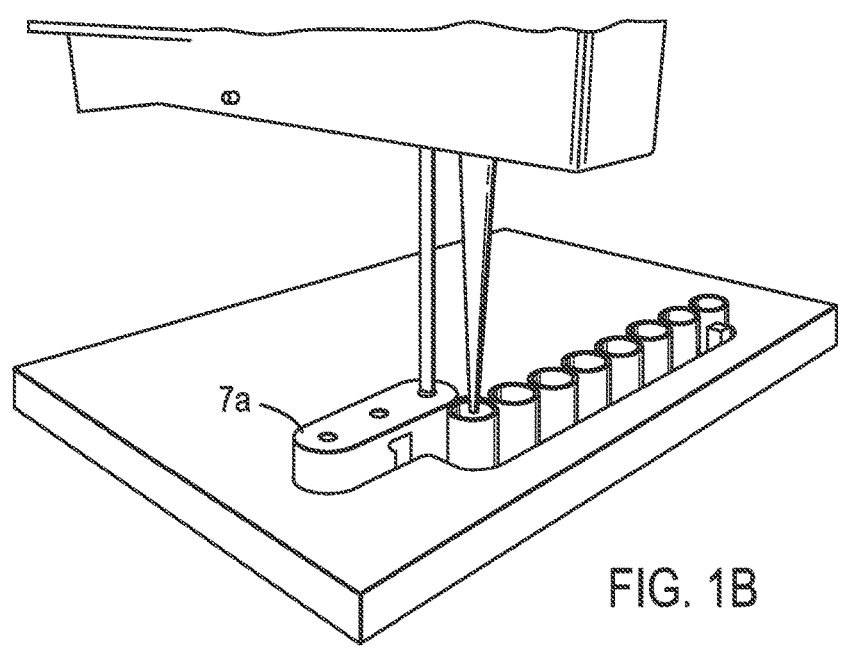
FIG. 1B is an additional view of the device shown in FIG. 1A. This view features a slide block 7 in an OUT position.
Figure 1C:
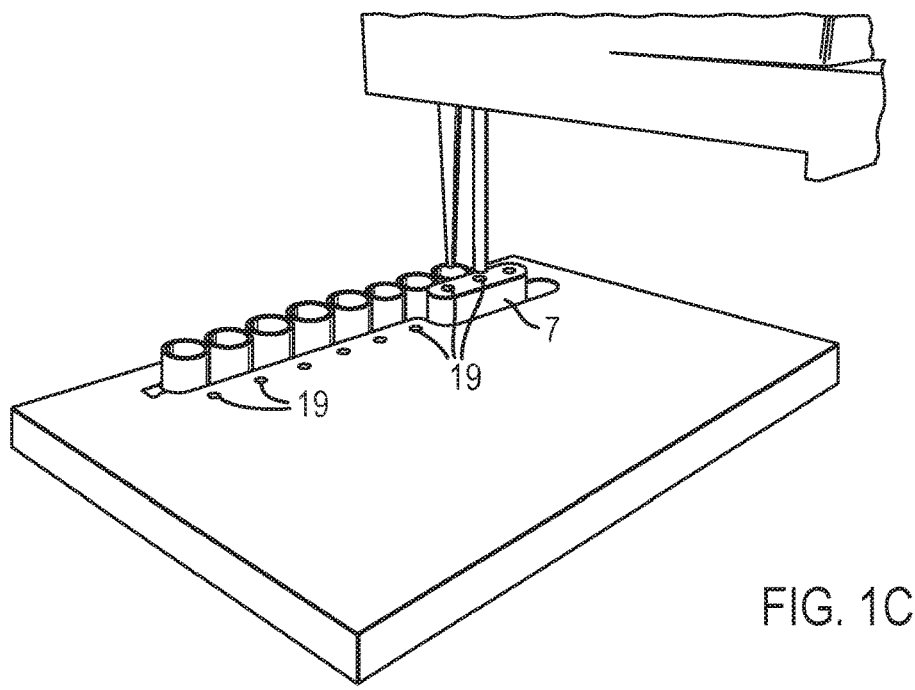
FIG. 1C is a rear view of the device shown in FIG. 1A. This view features the holes 9 designed to accommodate a control rod 8.

One embodiment of the automated sample handling device of the present teachings is partially illustrated in FIGS. 1A, 1B and 1C. The embodiment includes a platform 4 holding one X×Y array 3, where (as shown) X is 1 and Y is 8, alternatively referred to as one eight site strip, preloaded with a magnetic fraction sample to be separated and any reagents/solutions used in the automated process. The embodiment may also include an arm (e.g., a mechanical stage or arm) 11 holding a pipette 2, connected to a pump (for example, pump 22 illustrated in FIG. 3A) and an electronic control unit (for example, control unit 20 illustrated in FIG. 3A) including a processer and memory encoding one or more programs. The control unit is adapted to cause the mechanical stage or arm and pump to carry out various tasks. The mechanical stage or arm is adapted to pick up the pipette; position the pipette at any of the plurality of sites and engage the transfer device with a liquid material at that site. The mechanical stage or arm is also adapted to use the control rod 8 to engage the slide block 7 to position the magnet 5 in an IN or an OUT (see, FIG. 1B, 7a) position so that a sample is at a separation site such that the sample is either within a magnetic field of the magnet or is sufficiently distant so as not to affect the magnetic fraction in the sample at the separation site. A second magnet 6 is located at the opposite end of the 1×8 array and serves to capture any beads that may have been transferred to the last well. A rear perspective illustrated in FIG. 1C shows holes 19 to accommodate control rod while pipetting.

Figure 2:
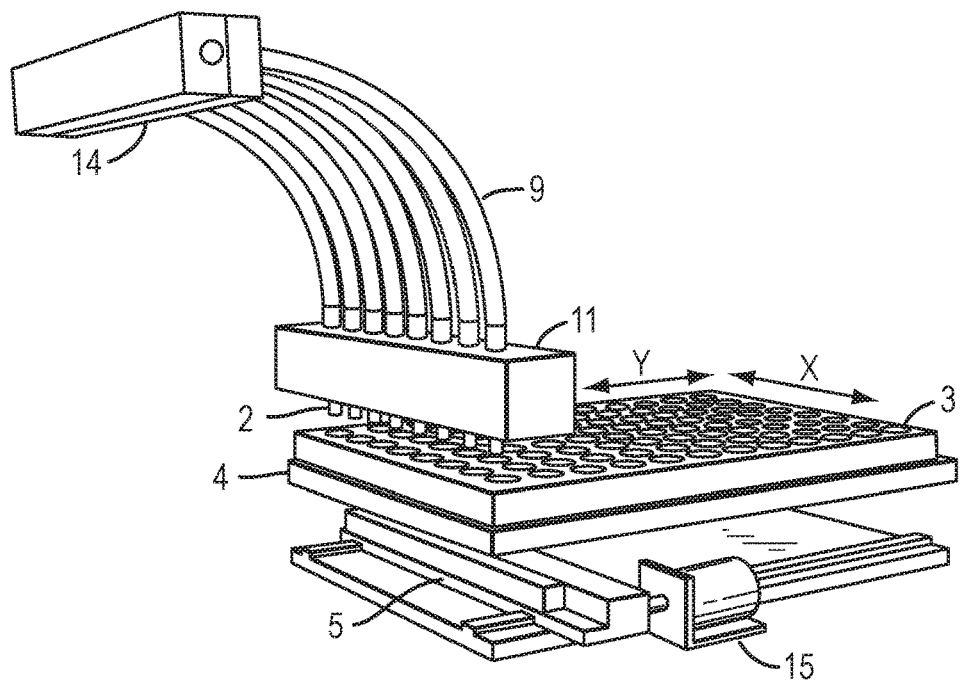
FIG. 2 is a perspective view of an automated sample handling system for conducting automated sample preparation according to various embodiments of the present teachings.

Another embodiment the automated sample handling device of the present teachings is partially illustrated in FIG. 2. The embodiment is capable of multi-channel sample handling and includes a platform 4 holding a two dimensional array where each dimension is greater than 1, for example, an X×Y array of sites 3 where X is 8 and Y is 12.

Alternatively, the array of sites may be described as X of 1×Y strips, e.g., eight 1×12 strips. The sites/strips may or may not be attached to each other. Each array or strip may be preloaded with samples containing a magnetic fraction to be separated and any reagents/solutions used in the automated process. The embodiment may also include an arm (e.g., a mechanical stage or arm) 11 holding an array of pipette tips 2 each connected to a manifold 14 by tubing segments 9. The manifold 14 may be connected to a pump (for example, pump 22 illustrated in FIG. 3A) and a control unit (for example, control unit 20 illustrated in FIG. 3A) including a processor and memory encoding one or more programs. Various embodiments may also include reagent bottles wherein the pump is adapted to deliver the contents of the reagent bottles to a plurality of sites. Alternatively, or in addition, the embodiment may include a reservoir adapted receive contents aspirated from at least one of a plurality of sites. The embodiment may further include a bar magnet 5 that extends the X direction (as indicated in the figure) and spans all of the sample strips. The bar magnet is positioned at either an IN position or an OUT position by an actuator 15. A second magnet 6 (not pictured) may optionally be located at the opposite end of the 8×12 array as magnet 6 and serves to capture any beads that may have been transferred to the last well.

In various embodiments, the method according to the present teachings may be carried out as follows using a two dimensional array with X by Y number of sites, where X corresponds to the number of samples to be manipulated by one automated process and where Y number of sites is 8. The apparatus according to the present embodiment includes an array of tips, e.g., for aspirating/dispensing/transferring, where the number of tips corresponds to the number of wells in the X dimension of the array. Embodiments of the automated sample handling device of the present teachings such as the one partially illustrated in FIG. 2 may be particularly well suited for performing the following method. The apparatus may also include reagent bottles and a pump adapted to deliver the contents of the reagent bottles to a plurality of sites. The user connects all bottles and reservoirs, e.g., waste bottle and bottles containing wash solution and water. The user also loads samples and primary reagents into wells and loads the array, which may be a plate or strip. Then the apparatus of the present teachings is then set to perform the following sample manipulation sequence: 1) moving tip to Y position B then mixing solution via multiple aspirate/dispense cycles, 2) aspirating then transferring solution to Y position A wells, 3) mixing solutions at Y position A via multiple aspirate/dispense cycles 4) actuating magnet, then aspirating and transferring solution to Y position G wells (fail safe), 5) returning tip array to strip A, 6) de-actuating magnet, 7) dispensing wash solution and mix via multiple aspirate/dispense cycles, 8) actuating magnet then aspirating solution to waste reservoir, 9) repeating wash cycle as in steps 6, 7 and 8, 10) moving tip Y position F and aspirating, then transferring solution to Y position A wells, 11) de-actuating magnet and mixing solution via multiple aspirate/dispense cycles. After the above steps, the user collects the processed sample in Y position H wells.

In various embodiments of the present teachings, software may be programmed to execute the following commands: 'Get' which places the magnet in an IN position or turns the electromagnet on and 'return' which places the magnet in an OUT position or turns the electromagnet off; Go to Y position #; Aspirate x uL, where the user may input a volume, e.g., in an amount up to ~300 uL in ~10 uL increments; Dispense x uL, where the user may input a volume, e.g., in an amount up to ~300 uL in ~10 uL increments; Aspirate/dispense speed, where the user may input a speed e.g., ~50 to 500 uL/sec in ~50 uL/sec increments; Hold/delay where the user may input a time period, e.g., 0-150 seconds, 5 second increments. Variables available for user input also include parameters for the mixing step: Number of cycles, Aspirate/dispense volumes, Aspirate speed, dispense speed, Hold/delay time between each cycle, Aspirate height, Dispense height. Volume accuracy: ~5 uL. Generally, the following variables are also set: Min volume/transfer: ~100 uL, Max volume/transfer: ~250 uL, Tip/nozzle positional accuracy: ~1 mm in X & Y, ~0.1 mm in Z, Magnet positional accuracy: ~1 mm in X & Y and Z, Temporal accuracy: ~1 second. The values may be adapted in accordance with the requirements of any of a variety of sample handling procedures and are not intended to be limiting. Other variables that considered useful for any of a variety of procedures may also be included in the software and available for input by the user.

Figure 3A:
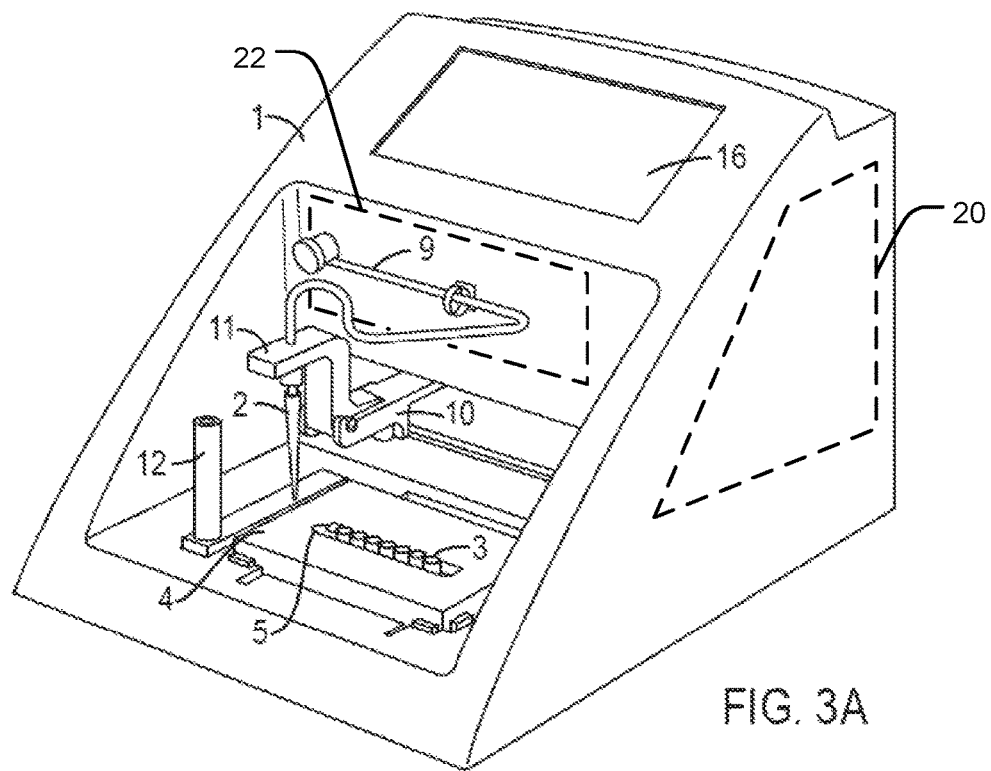
FIG. 3A is a perspective view of an automated sample handling system for conducting automated sample preparation according to various embodiments of the present teachings.
Figure 3B:
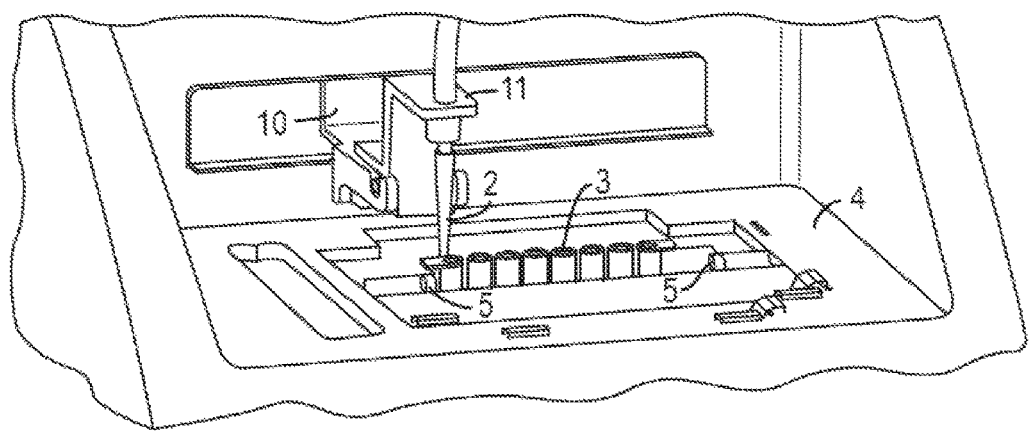
FIG. 3B is an expanded view of the components of the system shown in FIG. 3A.
Figure 3C:
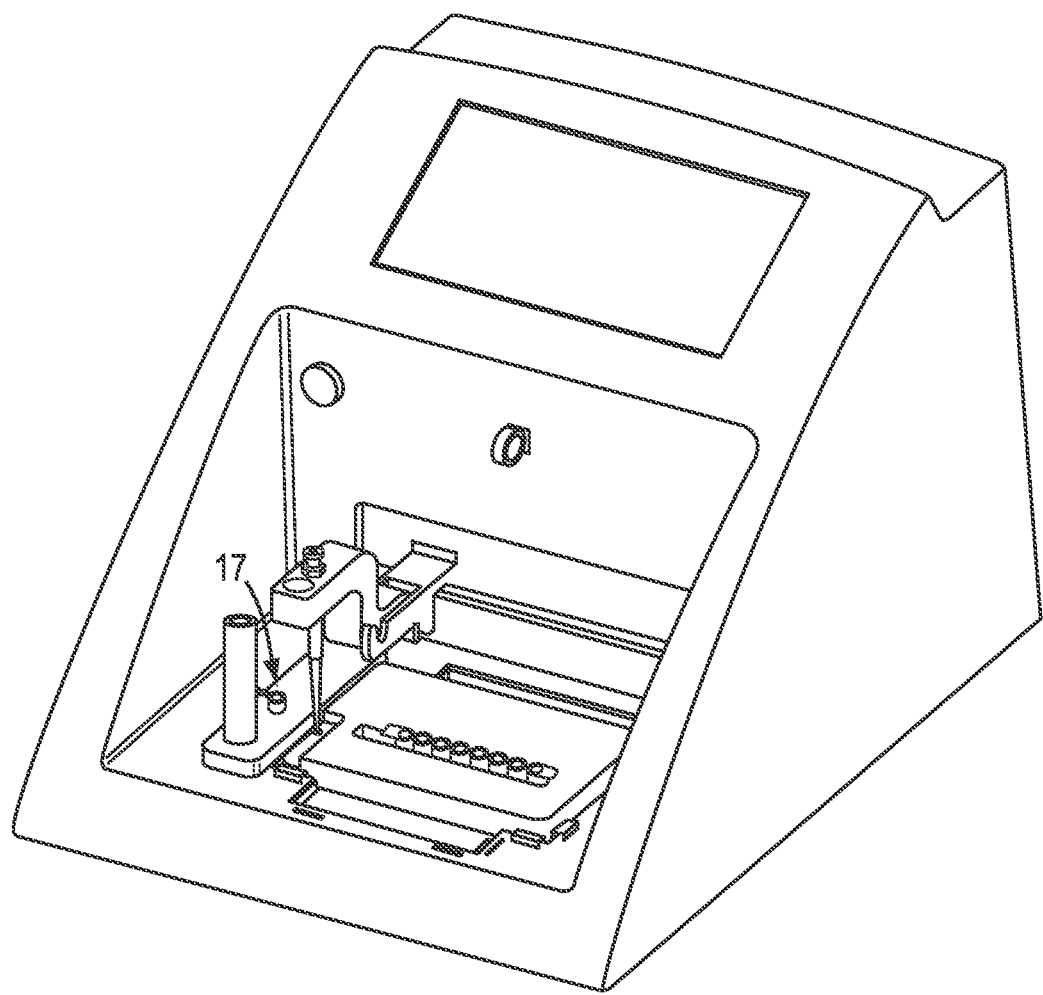
FIG. 3C shows a system having a receptacle for a container.

Another embodiment of the automated sample handling device of the present teachings 1 is partially illustrated in FIGS. 3A, 3B and 3C. The embodiment includes a platform 4 holding an X×Y array 3, where X is 1 and Y is 8 (alternatively referred to as one eight site strip) preloaded with a magnetic fraction sample to be separated and any reagents/solutions/material used in the automated process. The embodiment may also include an arm (e.g., a mechanical stage or arm) 11 for holding a pipette 2, and a tubing port 12 for detachable connection to pump 22 via tubing 9. The mechanical stage or arm may be detachably connected to a cradle 10 and may form a hinged joint there between. The mechanical stage or arm may be adapted to use the pipette to engage the array 3 to position the sample in an IN or an OUT position such that the sample at a separation site is either within a magnetic field or is sufficiently distant so as not to affect the magnetic fraction in the sample at the separation site, respectively.

The apparatus of the present teachings may further include a receptacle for a container to which a processed sample may be transferred. For example, the container may be a tube (e.g., a PCR tube). The receptacle may be placed at any suitable location in the apparatus as long as it can be reached by the device mounted on the mechanical stage. In some embodiments, the receptacle and the container 17 is disposed next to the holder for holding the device (FIG. 3c).

Figure 4:
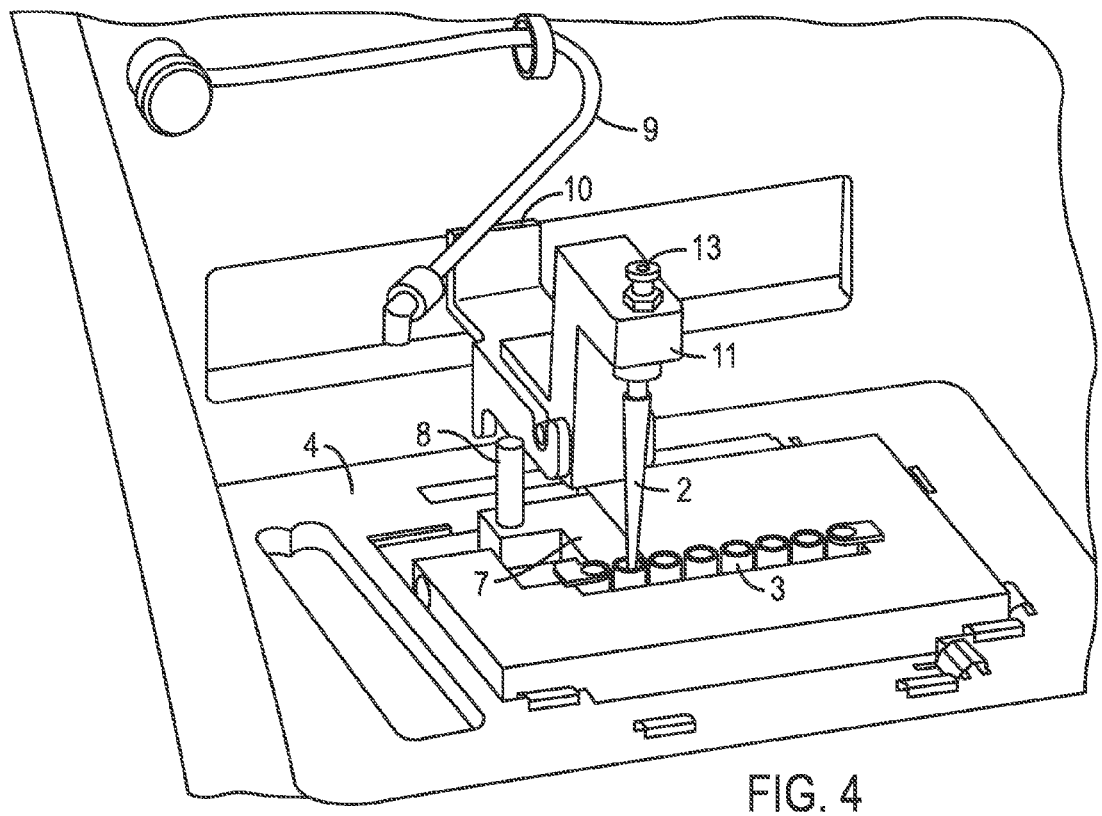
FIG. 4 is a perspective view of an automated sample handling system for conducting automated sample handling according to various embodiments of the present teachings.

Another embodiment of the automated sample handling device of the present teachings is partially illustrated in FIG. 4. The embodiment includes a platform 4 holding one X×Y array 3, where X is 1 and Y is 8, alternatively referred to as one eight site strip, preloaded with a magnetic fraction sample to be separated and any reagents/solutions/material used in the automated process. The embodiment may also include an arm (e.g., a mechanical stage or arm) 11 for holding a pipette 2, and has a tubing port 13 for detachable connection to a pump (not pictured) via tubing 9. The mechanical stage or arm may be detachably connected to a cradle 10 and may form a hinged joint there between. The mechanical stage or arm may be adapted to use the control rod 8 to engage the slide block 7 to position the magnet 5 in an IN or an OUT position where the sample at a separation site is either within a magnetic field or is sufficiently distant so as not to affect the magnetic fraction in the sample at the separation site, respectively. Alternatively or additionally, an actuator or solenoid (not pictured) may be used to position the magnet 5 in an IN or OUT position. A second magnet 6 (not pictured) may be located at the opposite end of the array and serves to capture any beads that may have been transferred to the last well.

Figure 5:
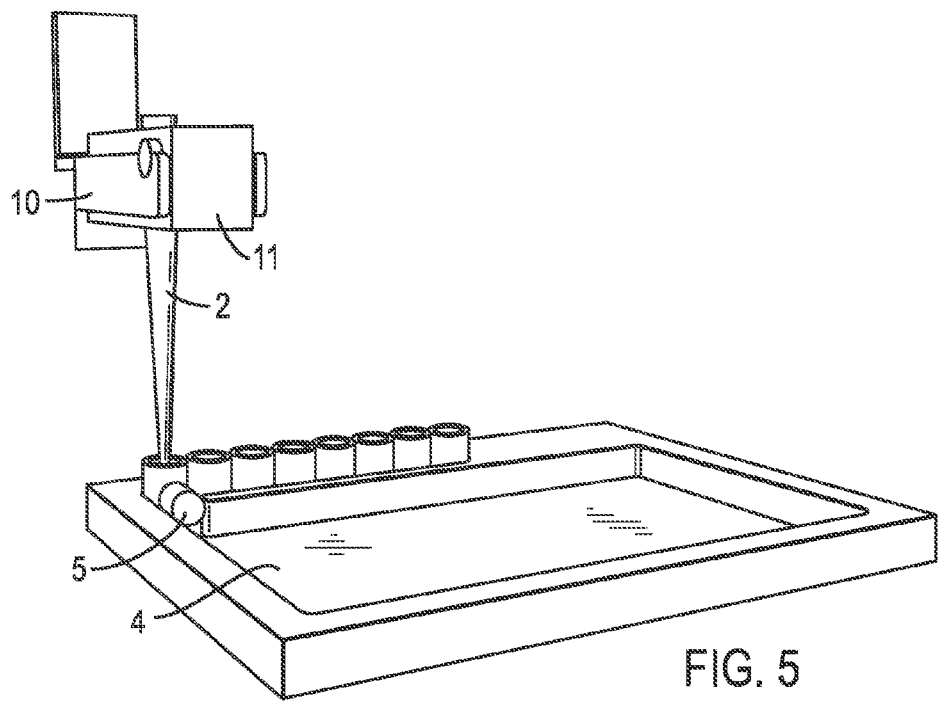
FIG. 5 is a perspective view of an automated sample handling system for conducting automated sample handling according to various embodiments of the present teachings.

Another embodiment of the automated sample handling device of the present teachings is partially illustrated in FIG. 5. The embodiment includes a platform 4 holding one X×Y array 3, where X is 1 and Y is 8, alternatively referred to as one eight site strip, which may be preloaded with a magnetic fraction sample to be separated and any reagents/solutions/material used in the automated process. The embodiment may also include an arm (e.g., a mechanical stage or arm) 11 for holding a pipette 2, and may optionally have a tubing port 13 for detachable connection to a pump via tubing 9. Alternatively, the pipette may be connected to an automatic volumetric pipette operated by a piston or the like. The mechanical stage or arm may be detachably connected to a cradle 10 and may form a hinged joint there between. The mechanical stage or arm may be adapted to position the pipette at any of the plurality of sites and engage the transfer device with a liquid material at that site. The mechanical stage or arm may further be adapted to pick up the pipette. An actuator or solenoid may be used to position the magnet 5 in an IN or an OUT position where the sample at a separation site is either within a magnetic field or is sufficiently distant so as not to affect the magnetic fraction in the sample at the separation site, respectively. A second magnet 6 (not pictured) may be located at the opposite end of the array and serves to capture any beads that may have been transferred to the last well.

In a first aspect, an apparatus for automated liquid sample manipulation includes an array of compartments, a magnet, a translation device including a mounting for a pipette tip, and a control unit to facilitate relative movement of the array and the magnet to apply and remove a magnetic field from at least one compartment of the array. The control unit is to control the translation device to position the pipette tip in the at least one compartment.

In an example of the first aspect, the magnet is movable, the control unit to facilitate movement of the magnet into and out of proximity to the at least one compartment of the array. For example, the control unit is to control the translation device to move the magnet. In an example, the translation device includes a rod and the magnet is disposed within a movable sled configured to receive the rod. In a further example, the magnet is disposed within a movable sled having a rod, the translation to engage the rod to move the sled.

In another example of the first aspect and the above examples, the magnet is stationary and the array of compartments is movable, the control unit to control the translation device to move the at least one compartment into proximity with the magnet. For example, the apparatus further includes a platform including a channel to receive the array of compartments, the array of compartments movable along the channel.

In a further example of the first aspect and the above examples, the apparatus includes a pump in communication with the pipette tip to facilitate aspiration and deposition of fluids.

In an additional example of the first aspect and the above examples, the array of compartments is a strip of tubes.

In another example of the first aspect and the above examples, the array of compartments is a tray of wells.

In a second aspect, an apparatus includes a platform to receive an array of compartments, a magnet in proximity to the platform, a translation device including a mounting for a pipette tip, and a control unit to facilitate relative movement of the array and the magnet to apply and remove a magnetic field from at least one compartment of the array. The control unit is to control the translation device to position the pipette tip in the at least one compartment.

In an example of the second aspect, the magnet is movable, the control unit to facilitate movement of the magnet into and out of proximity to the at least one compartment of the array. For example, the control unit is to control the translation device to move the magnet. In another example, the translation device includes a rod and the magnet is disposed within a movable sled configured to receive the rod. In an additional example, the magnet is disposed within a movable sled having a rod, the translation to engage the rod to move the sled.

In another example of the second aspect and the above examples, the magnet is stationary and the array of compartments is movable relative to the platform, the control unit to control the translation device to move the at least one compartment into proximity with the magnet. For example, the platform includes a channel to receive the array of compartments, the array of compartments movable along the channel.

In a further example of the second aspect and the above examples, the apparatus further includes a pump in communication with the pipette tip to facilitate aspiration and deposition of fluids.

In an additional example of the second aspect and the above examples, the array of compartments is a strip of tubes.

In another example of the second aspect and the above examples, the array of compartments is a tray of wells.

In a third aspect, a method for enriching templated beads includes forming a complex including a magnetic enrichment bead and a templated bead, applying a magnetic field to the complex to secure the complex, washing the complex, and separating the templated bead from the magnetic enrichment bead.

In an example of the third aspect, separating the template bead from the magnetic enrichment bead includes breaking the complex into a separate magnetic enrichment bead and a template bead, applying a magnetic field to secure the separate magnetic enrichment bead, and removing the template bead.

In another example of the third aspect and the above examples, applying the magnetic field includes moving a magnet into position adjacent a tube including the complex.

In an additional example of the third aspect and the above examples, applying the magnetic field includes moving a tube including the complex into position adjacent a magnet.

In a further example of the third aspect and the above examples, applying the magnetic field includes activating an electromagnet adjacent a tube including the complex.

In a fourth aspect, a method of enriching templated beads includes mixing a dispersion of templated beads with magnetic enrichment beads in a well to form complexes including at least one templated bead and at least one magnetic enrichment bead, applying a magnetic field to the container to secure the complexes to a wall of the well, washing the well with a wash solution, and removing the magnetic field.

In an example of the fourth aspect, the method further includes separating the templated beads from the complexes, applying a magnetic field to secure the magnetic enrichment beads, and removing the templated beads from the well.

In another example of the fourth aspect and the above examples, applying the magnetic field includes moving a magnet into position adjacent the well including the complexes.

In a further example of the fourth aspect and the above examples, applying the magnetic field includes moving the well including the complexes into position adjacent a magnet.

In an additional example of the fourth aspect and the above examples, applying the magnetic field includes activating an electromagnet adjacent the well including the complexes.

For the purposes of this specification and appended claims, unless otherwise indicated, all numbers expressing quantities, percentages or proportions, and other numerical values used in the specification and claims, are to be understood as being modified in all instances by the term "about" or the symbol "~." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. An apparatus comprising:
   a horizontal platform including a channel to receive and hold a linear array of compartments in the channel, wherein the linear array of compartments is movable along the channel;
   a magnet disposed in the channel of the horizontal platform;
   a translation device including a mounting for a pipette tip, the pipette tip mounted to the mounting of the translation device; and
   a control unit configured to provide automated positioning of the linear array of compartments and the magnet and control the translation device to position the pipette tip in at least one compartment of the linear array of compartments.

2. The apparatus of claim 1, wherein the magnet is movable and the control unit is configured to provide automated positioning of the magnet relative to at least one compartment of the linear array of compartments.

3. The apparatus of claim 2, wherein the control unit is configured to control the translation device to move the magnet.

4. The apparatus of claim 3, wherein the translation device includes a rod; the apparatus further comprises a movable sled disposed in the channel and the movable sled is configured to receive the rod; and the magnet is disposed within the movable sled.

5. The apparatus of claim 3, further comprising a movable sled including a rod and the movable sled disposed in the channel; wherein the magnet is disposed within the movable sled; and the control unit is configured to control the translation device to engage the rod to move the movable sled.

6. The apparatus of claim 1, wherein the magnet is stationary and the control unit is configured to control the translation device to provides automated positioning of the linear array of compartments relative to the magnet.

7. The apparatus of claim 1, further comprising a pump in fluid communication with the pipette tip and connected to the control unit.

8. The apparatus of claim 1, wherein the linear array of compartments is a strip of tubes.

9. The apparatus of claim 1, wherein the linear array of compartments is a strip of wells.

10. The apparatus of claim 1, further comprising a second magnet proximal to a second end compartment of the linear array of compartments.

11. The apparatus of claim 6, wherein the control unit is configured to control the translation device to position the linear array of compartments within the channel with the pipette tip.

12. The apparatus of claim 7, wherein the control unit is configured to control the pump to provide automated volume displacement of fluids in the pipette tip.

13. The apparatus of claim 12, wherein the automated fluid displacement in the pipette tip has a volume accuracy of 5 µl (microliters).

14. The apparatus of claim 7, wherein the translation device includes a tubing port for a detachable tubing connection to the pump.

* * * * *